United States Patent [19]

Jörnéus et al.

[11] Patent Number: 4,824,372
[45] Date of Patent: Apr. 25, 1989

[54] APPARATUS FOR THE FIXATION OF A SINGLE-TOOTH RESTORATION

[75] Inventors: Lars Jörnéus; Lennart Lööf, both of Gothenburg; Bo Rangert, Mölnlycke, all of Sweden

[73] Assignee: Nobelpharma AB, Gothenburg, Sweden

[21] Appl. No.: 110,994

[22] Filed: Oct. 21, 1987

[30] Foreign Application Priority Data

May 13, 1987 [SE]  Sweden .............................. 8701949

[51] Int. Cl.$^4$ ............................................. A61C 13/00
[52] U.S. Cl. .................................................. 433/174
[58] Field of Search .......................... 433/173, 172, 174

[56] References Cited

U.S. PATENT DOCUMENTS 3,726,011  4/1973  Savignano ........................... 433/176
3,732,621  5/1973  Bostrom .............................. 433/176

*Primary Examiner*—Robert Peshock
*Attorney, Agent, or Firm*—Pollock, Vande Sande & Priddy

[57] ABSTRACT

The disclosure relates to an apparatus for the fixation of a single-tooth restoration to an implant in the form of an anchorage element (fixture) permanently anchored in the maxillary, comprising a substantially tubular spacer (4) which is anchored to the anchorage element by means of a spacer screw (5) provided with an externally threaded portion (23) which engages in an internally threaded recess (7) in the upper region of the fixture. The spacer screw (5) is provided with an unthreaded waist (25) whose length exceeds the thread diameter of the spacer screw, and has a screw head (20) of comparatively slight diameter and with a planar or gently conical shoulder which cooperates with a corresponding annular shoulder (19) in the tubular spacer (4). The apparatus is mounted in place by means of a double screwdriver whose one part fits the internal counterabutment in the spacer sleeve (4) and whose other part is caused to engage with the driver slot (24) of the screw head. In the mounting operation, equal, but counterdirected torques are applied to both parts of the screwdriver so that the implant will remain unloaded during the mounting operation proper.

8 Claims, 2 Drawing Sheets

4,824,372

APPARATUS FOR THE FIXATION OF A SINGLE-TOOTH RESTORATION

BACKGROUND OF THE INVENTION

The present invention relates to an apparatus for the fixation of a single-tooth restoration to an implant in the form of a fixture which is permanently anchored in the maxillary.

It is previously known in the art to permanently anchor oral and extraoral prostheses in bone tissue by means of screw-like anchorage elements, so-called fixtures, made of titanium. The method which was proved to give the highest anchorage stability and which has successfully been used clinically for more than 20 years is the so-called osseointegration method developed by professor PerIngvar Brånemark et al and described, for example, in:

Brånemark/Zarb/Albrektsson: "Tissue-Integrated Prostheses", Quintessence Books, 1985.

The method is based on a highly exact and atraumatic implant technique of the fixture such that a direct contact, in other words an exact adaptation without interjacent soft tissue, occurs between the fixture and the bone tissue. Such a direct contact between fixture and bone tissue provides the best preconditions for a really permanent fixation of, for example, a dental prosthesis.

The helicoid fixtures of pure titanium are operated into the maxillary in a first surgical operation which is followed by an unloaded healing phase of critical length during which the fixture is covered by intact mucous membrane. During this healing phase, the bone tissue grows into and forms a unit with the implanted fixture. In a second operation, the fixture is then exposed and a substantially tubular spacer is applied to the fixture by means of a spacer screw. Subsequently, the dental prosthesis for example—in the form of a bridge construction, is united to the fixture by means of a fixing screw which, in its turn, anchors in the spacer screw.

The development work which has hitherto been carried on in this art has, to a great extent, been concentrated on the surgical technique, see for example the above-mentioned publication "Tissue-Integrated Prostheses", and on the design of the fixture. Apart from a special surface structure and surface-chemical composition, it is, thus, important that the fixture be given an adequate, geometric design in order to more readily to satisfy the requirements of both atraumatic surgery and surface cleanliness. Swedish printed application No. 332 486 discloses a fixture in the form of a screw which is exteriorally threaded. The threaded portion of the screw is inserted in a threaded bore in the maxillary on permanent implantation of a dental prosthesis.

Swedish patent application No. 86.00611-1 also discloses a self-threading fixture which makes for a slightly simplified operation technique, but nevertheless satisfies all the requirements for osseointegration to be achieved. The fixture is designed as a cutting, self-threading tool which, in a single operational phase, is screwed into the pre-drilled seat. In this instance, a minor number of instruments are required for preparing the bone tissue, and in particular the prior art double-tap preparatory phases are eliminated.

While the osseointegration method provides uniquely advantageous properties with respect to anchorage stability and the risk of loosening or detachment, complications may, in certain cases, set in which entrain detachment tendencies. For example, extreme oral loadings, occlusion and chewing may entail the risk of detachment. Furthermore, incorrect surgical implantation of fixture and spacer may jeopardize the osseointegration. Consequently, to reduce the mechanical stresses involved, the dental prostheses are, as a rule, anchored by means of a bridge construction with the assistance of a plurality of fixtures, for example six (see further the publication "Tissue-Integrated Prostheses"). Should any of the fixtures display a tendency to loosen, the remainder will then ensure that the reliable overall anchorage is still maintained.

However, in recent years attempts have been made within this art to offer reliable anchorage of individual teeth, so-called single tooth restoration, see, for example, "Modified single and short-span restorations supported by osseointegrated fixtures in the partially edentulous jaw", by T. Jemt, The Journal of Prosthetic Denistry, Feb. 86, Vol. 55, No. 2. In such single-tooth restoration, one fixture alone should be able to withstand all of the oral loadings, such as the torque, flexion and compressive forces which may occur. The torque loading is of particular importance, as it strives to loosen the screw connection between the spacer screw and the fixture.

Naturally, for single-tooth restorations and the extreme oral stresses to which these may be exposed, it is of vital importance that the operation technique and the design of the fixture be of the optimum degree. However, it is also important that the design and anchorage of the spacer, or "abutment" as it is often called in this art, be of the best conceivable standard in order to prevent loosening of the screw connection.

SUMMARY OF THE PRESENT INVENTION

The object of the present invention is to provides a screw connection anchorage for a single-tooth restoration which exhibits increased anchorage stability as compared with prior art dental prosthesis of this type. According to the present invention the screw connection anchorage is designed so that the dental prosthesis shows but very slight tendency to loosen or detach, and has a great capacity for transmitting loadings.

As was mentioned above, the torque loading applied strives to loosen the screw connection between the spacer screw and the fixture. In order to attain the necessary torsion force, the pretensioning force in the spacer screw, the torque applied during the mounting operation must be converted and transferred as pretensioning force in the body of the screw in as favorable a manner as possible. This may be attained by reducing the moment of friction beneath the head of the spacer screw to a minimum. However, the spacer screws hitherto employed within the odontological art have been provided with conical shoulders which give rise to a large amount of friction. This also applies to single-tooth restoration in which the spacer screws have hitherto been provided with conical shoulders of an acute conical angle which, in many cases, may entail problems in single-tooth restoration. Futhermore, because of the conical angle, screws with conical shoulders beneath the head of the screw result in increased settling beneath the head of the screw, which increases the risk of detachment or dislocation, as compared with a screw with planar shoulder.

One particular object of the present invention is, therefore, to provide a screw connection anchorage in which the spacer screw provides reduced moment of friction and reduced settling beneath the head of the screw as compared with the prior art spacer screw.

Because of the torque loading, it is important that the spacer screw be fully tightened. In this instance, all of the tightening, or torque force will be imposed upon the fixture which then runs the risk of loosening unless particular measures are adopted, for example by the provision of an abutment, with the assistance of a specially-designed instrument for this purpose. However, such a method is extremely circumstantial and there is the risk that the fixture be overloaded such that the osseointegration process becomes jeopardized.

A further object of the present invention is, therefore, to design the screw connection anchorage in such a manner that the torque applied when the the spacer screw is tightened may be counteracted so that the fixture is not placed under any loading during the tightening operation.

To reduce long-term loosening or detachment tendencies in the fixture arising out of the torque load, the spacer should be capable of absorbing a certain elastic flexion. One manner of increasing the elastic flexion is to provide the spacer screw with a waist of a certain extent in the longitudinal direction of the shank of the screw, to which the elastic flexion is concentrated. Prior art spacer screws have not been provided with such a waist, or, in any event, the extent of such a waist in the longitudinal direction of the shank of the screw has proved to be wholly insufficient to truly provide the elastic flexion which is contemplated in single-tooth restoration.

A third object of the present invention is, to design the spacer screw to accommodate a considerably higher degree of elastic flexion than has hitherto been possible in prior art spacer screws.

The nature of the present invention and its aspects will be more readily understood from the following brief description of the accompanying Drawings, and discussion of one embodiment of the present invention relating thereto.

BRIEF DESCRIPTION OF THE ACCOMPANYING DRAWINGS

FIG. 1 is a section through an apparatus according to the present invention anchored to a helicoid anchorage element; and FIGS. 2 and 3 each illustrate their part of a double-purpose screwdriver adapted to the apparatus according to the present invention in order that the torque applied during the mounting operation shall not load the anchorage element (the fixture).

DESCRIPTION OF PREFERRED EMBODIMENT

Figure 1:
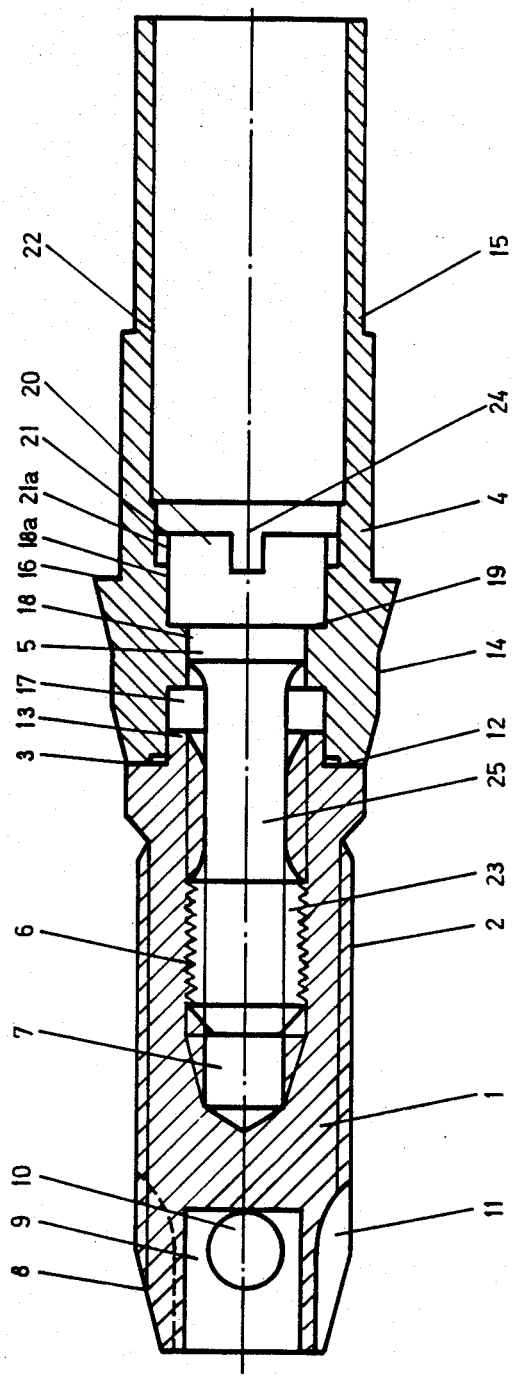

Referring to the drawings, FIG. 1 shows an apparatus according to the present invention anchored in an anchorage element in the form of a cylindrical screw (fixture) 1 of titanium, with an exterior thread 2 which is insertable into a predrilled hole in the maxillary for the permanent anchorage of a single-tooth restoration. Spacer means have been connected to the upper portion 3 of the fixture, these being in the form of a substantially fistular spacer sleeve 4 and a spacer screw 5 provided with a threaded portion 6 which engages with an interiorally threaded bore 7 in the upper portion of the fixture for fixedly anchoring the spacer sleeve 4 to the fixture.

The fixture has a downwardly conically tapering lower portion 8 so as to facilitate insertion of the fixture in the predrilled hole in the bone tissue. The fixture is provided with a drilled recess 9, apertures 10 being provided therein from the sides. The lower region of the fixture is further provided with a number, for example four, of flutes 11 whose ridges form cutting edges such that the screw is self-threading on anchorage in the bone tissue. The apertures 10 promote the healing of the fixture into the bone tissue, so that newly-formed bone tissue grow in through the holes, and the tendency for unscrewing of the fixture after its implantation will be effectively prevented.

The upper region 3 of the fixture displays a planar, annular shoulder 12 against which the end portion of the spacer sleeve abuts, and a hexagonal engagement portion 13 to permit engagement of its associated tool for threading of the fixture into the predrilled hole in the maxillary.

The spacer sleeve 4 is provided with a lower, substantially conically tapering portion 14 for soft tissue penetration and an upper portion 15 which forms a body or abutment for a single-tooth prosthesis. The upper portion 15 terminates at its bottom at the transition to the conical portion by a ledge 16 against which the base portion of the dental prosthesis is intended to abut.

The conical portion 14 of the spacer sleeve is provided, at its bottom, with an interiorally hexagonal recess 17 which cooperates with the engagement portion 13 of the fixture. This recess merges at its top into a narrower cylindrical portion 18 provided with a planar, annular shoulder 19 against which the lower, planar surface of the head 20 of the spacer screw abuts. The narrower, or waisted, portion 18 subsequently merges, through shoulder 19, into a larger cylindrical portion 18a provided to accommodate the head of the spacer screw. The cylindrical portion 18a merges in turn through a further narrow annular shoulder 21 into a broader cylindrical upper portion 22. Contrary to prior art spacer screws employed in odontology, the diameter of the screw head 20 is slight, for example exceeding the diameter of the outer thread of the screw by 20–30 percent. The screw head has a cylindrical circumferential surface and planar shoulder, which is also in contrast to prior art spacer screws which have conical shoulders with an acute conical angle. As a result of the novel structure of the present invention device, the moment of friction beneath the screw head is reduced, which makes for a more favorable translation of the applied torque into prestressing force in the screw shank. The screw head need not have a completely planar shoulder. A slightly conical shoulder, for example, a shoulder making an obtuse conical angle, will also make for reduced moment of friction as compared with prior art spacer screws. The spacer screw is provided with a threaded male portion 23 which engaged with the interior threading in the fixture in the recess 7. A driver slot 24 is provided in the screw head 20 for threading in the spacer screw.

Contrary to prior art spacer screws, the screw according to the present invention is also provided with an unthreaded waist 25 (non thread-loaded section) whose length at least exceeds the thread diameter of the screw. The diameter of the waist corresponds substantially to the diameter of the interior threading on the threaded portion. The non thread-loaded portion of the screw contributes to increasing the elastic flexion ability of the screw, which reduces the risk of long-term loosening or detachment tendencies on the part of the implant. As an alternative to the waist 25 on the spacer screw, the recess 7 in the fixture may be provided with a free bore whose length is to exceed the thread pitch, in the same manner as the waist.

Figure 2:
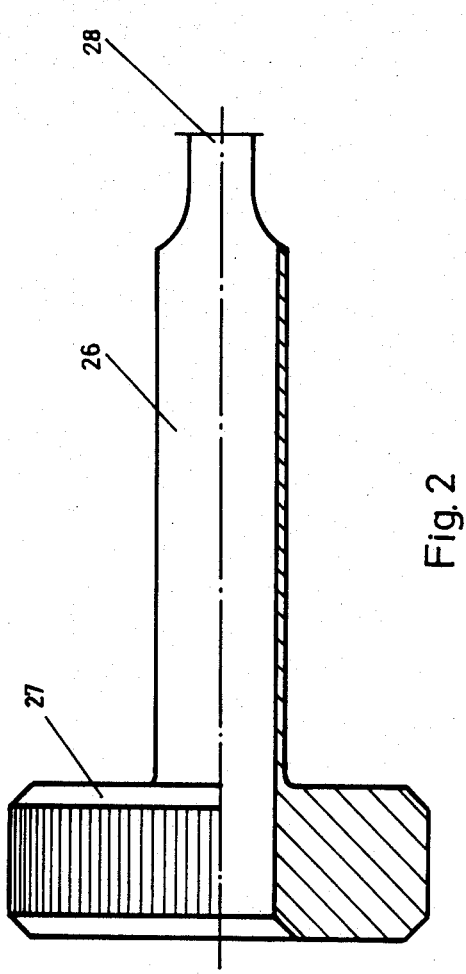

As was mentioned by way of introduction, single-tooth restorations, are particularly exposed to torque loadings and it is, therefore, important that the screw be fully tightened. In order that the entire tightening moment of energy should not load the fixture, the spacer sleeve is provided with an interior counter-abutment in the form of two diametrically disposed recesses 21a in the annular shoulder 21 where one portion (see FIG. 2) of a double screwdriver adapted to this purpose will fit. This part includes a tubular shaft which fits into the upper interior portion 22 of the spacer, and a handle 27. The tubular shaft 26 terminates at its bottom by two diametrically opposed shanks 28 which engage in the recess 21a between the exterior cylindrical circumferential surface of the screw head and the interior cylindrical surface of the spacer sleeve.

Figure 3:
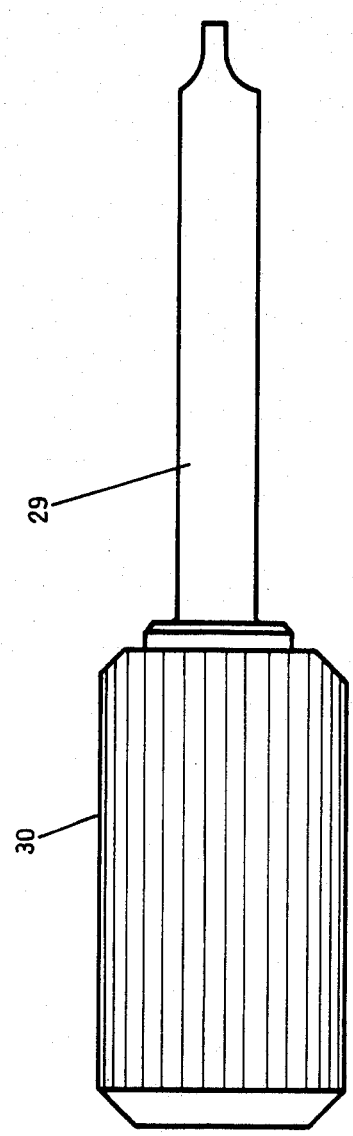

The second portion (see FIG. 3) of the double screwdriver consists of a solid shaft 29 which fits within the tubular shaft 28 of the first screwdriver, and a narrow, somewhat elongate handle 30. The second screwdriver portion is designed as a conventional screwdriver and fits in the driver slot 24 in the head of the spacer screw.

The apparatus is used as follows. First, a section is made in the periodontal tissue, thus exposing the maxillary. The anchorage element (the fixture) 1 is then surgically implanted in the maxillary using previously known, atraumatic operation techniques. A fixing screw (not shown) is then applied to the upper bore 7 of the fixture, whereafter the fixture is covered by the periodontal tissue and the fixture is left for an unloaded healing phase of 3-6 months to grow to the maxillary.

In a second operation, after the above-mentioned healing phase, the fixture 1 is exposed, the covering screw is removed and is replaced by the spacer members. The selection and testing of each individual prosthesis is not germane to the present invention and will not, therefore, be described in greater detail here. This disclosure will relate solely to the application of the spacers. The spacer sleeve 4 is applied to the upper region 3 of the anchorage element such that the end portion of the sleeve abuts against the annular shoulder 12 of the anchorage element. In this position, the lower region of the sleeve abuts against the hexagonal engagement portion 13 of the fixture and cannot be rotated in relation to the fixture. The spacer sleeve 4 is locked in position against the fixture by means of the spacer screw 5 which is screwed down into the bore 7 in the fixture by means of the double screwdriver, it being ensured in this operation that the shanks 28 of the tubular portion engage with the recesses 21a in the spacer sleeve. The second portion of the screwdriver is passed through the tubular portion so as to engage in the driver slot in the head 20 of the spacer screw. On mounting of the screw connection, equal, but counter-directed, torques are applied to both of the screwdriver portions, the implant remaining unloaded during the mounting procedure proper.

The present invention should not be considered as restricted to that described above and shown on the Drawings, many modifications being conceivable without departing from the spirit and scope of the appended claims.

What we claim and desire to secure by Letters Patent is:

1. An apparatus for anchoring a single-tooth restoration to an implant fixture permanently anchored in the maxillary and having an internally threaded bore in the upper portion of the fixture, said apparatus comprising:
    a tubular spacer member having an outer wall for connecting to the single-tooth restoration and an annular internal inwardly extending shoulder provided along an inner wall of a lower portion of said spacer member;
    a screw member insertable into said tubular spacer for connecting said tubular spacer member to the implant fixture, said screw member including:
    a lower externally threaded portion at one end thereof, screwable into the internally threaded portion of the fixture;
    a substantially cylindrical head portion on the opposite end thereof provided with a corresponding outwardly extending substantially planar shoulder which cooperates with said annular shoulder on said tubular spacer member for connecting said spacer member to said screw member; and
    a non-thread loaded portion having a length larger than the thread diameter of said threaded portion.

2. Apparatus according to claim 1, wherein said screw head (20) is of a substantially small diameter to provide high abutment pressure of said screw head and minimize moment of friction beneath said screw head (20).

3. Apparatus according to claim 2 wherein said screw head (20) has a substantially cylindrical circumferential surface and is disposed in a corresponding cylindrical bore (18a) in said tubular spacer member, the diameter of said screw head exceeding the diameter of the exteriorly threaded portion of said screw by about 20 to about 30 percent.

4. Apparatus according to claim 1, wherein said tubular spacer member (4) is provided with an interior, internal counter-abutment in the form of an annular shoulder (21) into which one portion of a double screwdriver for fixedly screwing said spacer screw (5) is insertable, the other portion of said screwdriver cooperating with a driver slot (24) disposed in the screw head (20) of said spacer screw.

5. Apparatus according to claim 4 wherein recesses (21a) are formed and diametrically disposed and formed in said annular shoulder (21) between cylindrical portion (18a) which accomodates the screw head (29) of said spacer screw, and an upper, wider cylindrical portion (22) in said tubular spacer member.

6. Apparatus according to claim 1, wherein said non-threaded loaded portion includes an inthreaded waist (25) having diameter smaller than the diameter of the interior thread on the threaded portion (26) of said spacer screw.

7. Apparatus according to claim 1 wherein said non-threaded loaded portion includes a free bore of the interior thread in the recess (7) in the upper region of said anchorage element.

8. An apparatus for fixedly anchoring a single-tooth restoration to an implant in the form of an anchorage element (fixture) permanently anchored in the maxillary, comprising:
    a substantially tubular spacer member having an internal annular shoulder in a lower portion of said spacer member, said spacer member being anchored to the fixture by means of a spacer screw, said spacer screw having a lower part to be inserted in the upper region of the fixture and an upper part with a screw head, said lower part of the spacer screw including an exteriorly threaded portion which engages in an interiorly threaded bore in an upper region of said fixture for threading in the spacer screw and non-thread loaded portion whose length exceeds the thread diameter of said threaded portion; and wherein said screw head is provided with a substantially planar shoulder which cooperates with said annular shoulder in the tubular spacer member.

* * * * *